US009617596B2

(12) United States Patent
Comabella et al.

(10) Patent No.: US 9,617,596 B2
(45) Date of Patent: Apr. 11, 2017

(54) BIOMARKERS PREDICTIVE FOR CLINICAL RESPONSE FOR GLATIRAMER ACETATE

(71) Applicants: Manuel Comabella, Barcelona (ES); Xavier Montalban, Barcelona (ES)

(72) Inventors: Manuel Comabella, Barcelona (ES); Xavier Montalban, Barcelona (ES)

(73) Assignee: TEVA PHARMACEUTICAL INDUSTRIES, LTD., Petach-Tikva (IL)

(*) Notice: Subject to any disclaimer, the term of this patent is extended or adjusted under 35 U.S.C. 154(b) by 385 days.

(21) Appl. No.: 14/050,195

(22) Filed: Oct. 9, 2013

(65) Prior Publication Data
US 2014/0107208 A1 Apr. 17, 2014

Related U.S. Application Data

(60) Provisional application No. 61/712,146, filed on Oct. 10, 2012.

(51) Int. Cl.
*C12Q 1/68* (2006.01)

(52) U.S. Cl.
CPC ......... *C12Q 1/6881* (2013.01); *C12Q 1/6883* (2013.01); *C12Q 2600/106* (2013.01); *C12Q 2600/158* (2013.01)

(58) Field of Classification Search
CPC ............... C12Q 1/6881; C12Q 1/6883; C12Q 2600/106; C12Q 2600/158
See application file for complete search history.

(56) References Cited

U.S. PATENT DOCUMENTS

| | | | |
|---|---|---|---|
| 3,849,550 A | 11/1974 | Teitelbaum at al. | |
| 5,800,808 A | 9/1998 | Konfino et al. | |
| 5,981,589 A | 11/1999 | Konfino et al. | |
| 6,048,898 A | 4/2000 | Konfino et al. | |
| 6,054,430 A | 4/2000 | Konfino et al. | |
| 6,214,791 B1 | 4/2001 | Arnon et al. | |
| 6,342,476 B1 | 1/2002 | Konfino et al. | |
| 6,362,161 B1 | 3/2002 | Konfino et al. | |
| 6,514,938 B1 | 2/2003 | Gad et al. | |
| 6,620,847 B2 | 9/2003 | Konfino et al. | |
| 6,800,285 B2 | 10/2004 | Rodriguez et al. | |
| 6,800,287 B2 | 10/2004 | Gad et al. | |
| 6,939,539 B2 | 9/2005 | Konfino et al. | |
| 7,022,663 B2 | 4/2006 | Gilbert et al. | |
| 7,033,582 B2 | 4/2006 | Yong et al. | |
| 7,074,580 B2 | 7/2006 | Gad et al. | |
| 7,163,802 B2 | 1/2007 | Gad et al. | |
| 7,199,098 B2 | 4/2007 | Konfino et al. | |
| 7,279,172 B2 | 10/2007 | Aharoni et al. | |
| 7,425,332 B2 | 9/2008 | Aharoni et al. | |
| 7,429,374 B2 | 9/2008 | Klinger | |
| 7,495,072 B2 | 2/2009 | Dolitzky | |
| 7,560,100 B2 | 7/2009 | Pinchasi et al. | |
| 7,566,767 B2 | 7/2009 | Strominger et al. | |
| 7,615,359 B2 | 11/2009 | Gad et al. | |
| 7,625,861 B2 | 12/2009 | Konfino et al. | |
| 7,855,176 B1 | 12/2010 | Altman et al. | |
| 7,923,215 B2 | 4/2011 | Klinger | |
| 7,968,511 B2 | 6/2011 | Vollmer et al. | |
| 8,008,258 B2 | 8/2011 | Aharoni et al. | |
| 8,232,250 B2 | 7/2012 | Klinger | |
| 8,367,605 B2 | 2/2013 | Konfino et al. | |
| 8,389,228 B2 | 3/2013 | Klinger | |
| 8,399,211 B2 | 3/2013 | Gad et al. | |
| 8,399,413 B2 | 3/2013 | Klinger | |
| 8,709,433 B2 | 4/2014 | Kasper | |
| 8,759,302 B2 | 6/2014 | Dhib-Jalbut | |

(Continued)

FOREIGN PATENT DOCUMENTS

| | | |
|---|---|---|
| WO | WO 95/31990 | 11/1995 |
| WO | WO 98/30227 | 7/1998 |

(Continued)

OTHER PUBLICATIONS

Erin L. Heinzen, Dongliang Ge, Kenneth D. Cronin, Jessica M. Maia, Kevin V. Shianna, Willow N. Gabriel, Kathleen A. Welsh-Bohmer, Christine M. Hulette, Thomas N. Denny, David B. Goldstein, Tissue-Specific Genetic Control of Splicing: Implications for the Study of Complex Traits, PLoS Biology, Dec. 2008 | vol. 6 | Issue 12 | e1000001.*
Louise Gagnon, Every-Other-Day Dosing of Glatiramer Acetate Reduces Adverse Reactions With Comparable Efficacy to Daily Dosing: Presented at WCTRMS, Peer View Press, Sep. 21, 2008.*
U.S. Appl. No. 14/630,326, filed Feb. 24, 2015 (Klinger).
U.S. Appl. No. 11/228,850, filed Sep. 14, 2005 (Schwartz et al.). The specification and claims as originally filed.
U.S. Appl. No. 11/654,374, filed Jan. 16, 2007 (Schwartz et al.). The specification and claims as originally filed.
U.S. Appl. No. 09/359,099, filed Jul. 22, 1999 (Strominger et al.). The specification and claims as originally filed.
Reissue Application in connection with U.S. Appl. No. 13/964,856, filed Aug. 12, 2013 (Konfino et al.).

(Continued)

*Primary Examiner* — Sarah Pihonak
*Assistant Examiner* — Jason A Deck
(74) *Attorney, Agent, or Firm* — John P. White; Gary J. Gershik; Cooper & Dunham LLP

(57) ABSTRACT

The present invention provides a method for treating a human subject afflicted with multiple sclerosis or a single clinical attack consistent with multiple sclerosis with a pharmaceutical composition comprising glatiramer acetate and a pharmaceutically acceptable carrier, comprising the steps of:
  a) determining whether the human subject is a glatiramer acetate responder by evaluating expression of a biomarker selected from the group consisting of ERAP2, SIGLEC1, AAK1, KIAA1671, PLEKHA2, LOC730974, IFIT3, RWDD3, MYO6 SCARA3 and IFI44L, or a combination thereof, in human subject; and
  b) administering the pharmaceutical composition comprising glatiramer acetate and a pharmaceutically acceptable carrier to the human subject only if the human subject is identified as a glatiramer acetate responder.

19 Claims, 8 Drawing Sheets

(56) References Cited

U.S. PATENT DOCUMENTS

| | | |
|---|---|---|
| 8,815,511 B2 | 8/2014 | Tchelet et al. |
| 8,920,373 B2 | 12/2014 | Altman et al. |
| 8,969,302 B2 | 3/2015 | Klinger |
| 9,018,170 B2 | 4/2015 | Altman et al. |
| 9,063,153 B2 | 6/2015 | Kasper |
| 9,155,775 B1 | 10/2015 | Cohen et al. |
| 9,155,776 B2 | 10/2015 | Klinger |
| 2002/0077278 A1 | 6/2002 | Yong et al. |
| 2004/0156826 A1 | 8/2004 | Dangond et al. |
| 2005/0019322 A1 | 1/2005 | Rodriguez et al. |
| 2005/0170004 A1 | 8/2005 | Rosenberger |
| 2006/0172942 A1 | 8/2006 | Dolitzky |
| 2006/0240463 A1 | 10/2006 | Lancet |
| 2006/0264354 A1 | 11/2006 | Aharoni et al. |
| 2007/0021324 A1 | 1/2007 | Dolitzky |
| 2007/0037740 A1 | 2/2007 | Pinchasi et al. |
| 2007/0054857 A1 | 3/2007 | Pinchasi et al. |
| 2007/0059798 A1 | 3/2007 | Gad |
| 2007/0161566 A1 | 7/2007 | Pinchasi |
| 2007/0244056 A1 | 10/2007 | Hayardeny et al. |
| 2008/0118553 A1 | 5/2008 | Frenkel et al. |
| 2008/0207526 A1 | 8/2008 | Strominger |
| 2008/0261894 A1 | 10/2008 | Kreitman et al. |
| 2009/0048181 A1 | 2/2009 | Schipper et al. |
| 2009/0149541 A1 | 6/2009 | Stark et al. |
| 2010/0167983 A1 | 7/2010 | Kreitman et al. |
| 2010/0209914 A1* | 8/2010 | Bigwood ............ C12Q 1/6883 435/6.14 |
| 2010/0285600 A1 | 11/2010 | Lancet et al. |
| 2010/0298227 A1 | 11/2010 | Aharoni et al. |
| 2010/0305023 A1 | 12/2010 | Stark et al. |
| 2011/0053203 A1 | 3/2011 | D'Alessandro et al. |
| 2011/0060279 A1 | 3/2011 | Altman et al. |
| 2011/0066112 A1 | 3/2011 | Altman et al. |
| 2012/0020954 A1 | 1/2012 | Achiron et al. |
| 2012/0027718 A1 | 2/2012 | Kreitman et al. |
| 2012/0121619 A1 | 5/2012 | Kasper et al. |
| 2012/0309671 A1 | 12/2012 | Klinger |
| 2014/0107208 A1 | 4/2014 | Comabella et al. |
| 2014/0193827 A1 | 7/2014 | Schwartz et al. |
| 2014/0271532 A1 | 9/2014 | Kreitman et al. |
| 2014/0271630 A1 | 9/2014 | Vollmer |
| 2014/0294899 A1 | 10/2014 | Kasper et al. |
| 2014/0322158 A1 | 10/2014 | Dhib-Jalbut |
| 2015/0045306 A1 | 2/2015 | Tchelet et al. |
| 2015/0110733 A1 | 4/2015 | Tchelet et al. |
| 2015/0164977 A1 | 6/2015 | Klinger |
| 2015/0202247 A1 | 7/2015 | Klinger |
| 2015/0241446 A1 | 8/2015 | Kasper et al. |

FOREIGN PATENT DOCUMENTS

| | | |
|---|---|---|
| WO | WO 00/05250 | 2/2000 |
| WO | WO 00/05249 | 3/2000 |
| WO | WO 00/18794 | 4/2000 |
| WO | WO 00/20010 | 4/2000 |
| WO | WO 00/27417 | 5/2000 |
| WO | WO 01/60392 | 8/2001 |
| WO | WO 01/93828 | 12/2001 |
| WO | WO 01/97846 | 12/2001 |
| WO | WO 03/048735 | 6/2003 |
| WO | WO 2004/103297 | 2/2004 |
| WO | WO 2004/064717 | 8/2004 |
| WO | WO 2004/091573 | 10/2004 |
| WO | WO 2005/041933 | 5/2005 |
| WO | WO 2005/084377 | 9/2005 |
| WO | WO 2006/029036 | 3/2006 |
| WO | WO 2006/029393 | 3/2006 |
| WO | WO 2006/029411 | 3/2006 |
| WO | WO 2006/089164 | 8/2006 |
| WO | WO 2006/083608 | 9/2006 |
| WO | WO 2006/116602 | 11/2006 |
| WO | WO 2007/030573 | 3/2007 |
| WO | WO 2007/081975 | 7/2007 |
| WO | WO 2008/148115 | 12/2008 |
| WO | WO 2009/070298 | 6/2009 |
| WO | WO 2011/008274 | 1/2011 |
| WO | WO 2011/022063 | 2/2011 |
| WO | WO 2011/142824 | 11/2011 |
| WO | WO 2012/051106 | 4/2012 |
| WO | WO 2013/055683 | 4/2013 |
| WO | WO 2014/058976 | 4/2014 |
| WO | WO 2014107533 | 7/2014 |
| WO | WO 2014/165280 | 10/2014 |

OTHER PUBLICATIONS

Request for Ex Parte Re-examination by Third Party in connection with U.S. Control No. 90/013,249, filed May 21, 2014 (Konfino et al.).

Sep. 22, 2015 Official Action issued by the Bolivian Patent Office in connection with Bolivian Patent No. SP-0315-2013, including English language translation.

Sep. 29, 2015 First Examination Report issued by the New Zealand Patent Office in connection with New Zealand Patent Application No. 630421.

Blanco et al. "Effect of glatiramer acetate (CopaxoneR) on the immunophenotypic and cytokine profile and BDNF production in multiple sclerosis: A longitudinal study." Neuroscience Letters vol. 406, 2006, pp. 270-275.

Farina et al., "Immunological assay for assessing the efficacy of glatiramer acetate (Copaxone) in multiple sclerosis. A pilot study." J Neurol. Nov. 2002;249(11):1587-92.

Valenzuela, et al. "IL-27 Mediates Glatiramer Acetate Effect on Antigen Presenting Cells in Multiple Sclerosis", Neurology, vol. 74, No. 9, Suppl. 2, Mar. 2010 (Mar. 2010), p. A166, 62nd Annual Meeting of the American Academy of Neurology, Toronto, Canada, Apr. 10-17, 2010.

Zwibel "Glatiramer acetate in treatment-naive and prior interferon-beta-1b-treated multiple sclerosis patients", Acta Neurologica Scandinavica, vol. 113, No. 6, Jun. 1, 2006, pp. 378-386.

U.S. Appl. No. 14/520,280, filed Oct. 21, 2014 (Tchelet et al.).

International Search Report issued Apr. 4, 2014 in connection with PCT International Application No. WO2014/058976 (Comabella et al.).

Written Opinion of the International Searching Authority issued Apr. 4, 2014 in connection with PCT International Application No. WO2014/058976 (Comabella et al.).

International Search Report issued May 15, 2014 in connection with PCT International Application No. WO 2014/107533, (Schwartz et al.).

Written Opinion of the International Searching Authority issued May 15, 2014 in connection with PCT International Application No. WO 2014/107533 (Schwartz et al.).

Bakshi et al. "Gene expression analysis reveals functional pathways of glatiramer acetate activation" Expert Opin Ther Targets, 2013, 17(4):351-62.

Byun et al. "Genome-wide pharmacogenic analysis of the response to interferon beta therapy in multiple sclerosis" Arch Neurol. Mar. 2008; 65(3):337-44. Epub Jan. 14, 2008.

Fierabracci et al. "The putative role of endoplasmic reticulum aminopeptidases in autoimmunity: Insights from genomic-wide association studies" Autoimmunity Reviews, 2012, 13:281-288.

Grossman et al., "Pharmacogenetics of glatiramer acetate therapy for multiple sclerosis reveals drug-response markers" Pharmacogenetics and Genomics, 2007, 17: 657-666.

Hirschorn et al., "A comprehensive review of genetic association studies" Genetics in Medicine, Mar. 2002, 4(2): 45-61.

Ioannidis, et al. "Replication validity of genetic association studies" Nature Genetics, Nov. 2001, 29: 306-309.

Towfic et al. "Comparing the biological impact of glatiramer acetate with the biological impact of a generic" PLoS One, 2014, vol. 9, No. 1, pp. 1-11.

\* cited by examiner

BIOMARKERS PREDICTIVE FOR CLINICAL RESPONSE FOR GLATIRAMER ACETATE

This application claims benefit of U.S. Provisional Application No. 61/712,146, filed Oct. 10, 2012, the entire content of which is hereby incorporated by reference herein.

Throughout this application various publications are referenced by numerical identifiers in parentheses. Full citations of these references can be found following the Examples. The disclosures of these publications in their entireties are hereby incorporated by reference into this application in order to more fully describe the state of the art to which this invention pertains.

BACKGROUND OF THE INVENTION

Multiple sclerosis (MS) is a chronic, debilitating autoimmune disease of the central nervous system (CNS) with either relapsing-remitting (RR) or progressive course leading to neurologic deterioration and disability. At time of initial diagnosis, RRMS is the most common form of the disease (1) which is characterized by unpredictable acute episodes of neurological dysfunction (relapses), followed by variable recovery and periods of clinical stability. The vast majority of RRMS patients eventually develop secondary progressive (SP) disease with or without superimposed relapses. Around 15% of patients develop a sustained deterioration of their neurological function from the beginning; this form is called primary progressive (PP) MS. Patients who have experienced a single clinical event (Clinically Isolated Syndrome or "CIS") and who show lesion dissemination on subsequent magnetic resonance imaging (MRI) scans according to McDonald's criteria, are also considered as having relapsing MS.(2)

With a prevalence that varies considerably around the world, MS is the most common cause of chronic neurological disability in young adults.(3, 4) Anderson et al. estimated that there were about 350,000 physician-diagnosed patients with MS in the United States in 1990 (approx. 140 per 100,000 population).(5) It is estimated that about 2.5 million individuals are affected worldwide.(6) In general, there has been a trend toward an increasing prevalence and incidence of MS worldwide, but the reasons for this trend are not fully understood.(5)

Current therapeutic approaches consist of i) symptomatic treatment ii) treatment of acute relapses with corticosteroids and iii) treatment aimed to modify the course of the disease. Currently approved therapies target the inflammatory processes of the disease. Most of them are considered to act as immunomodulators but their mechanisms of action have not been completely elucidated. Immunosuppressants or cytotoxic agents are also used in some patients after failure of conventional therapies. Several medications have been approved and clinically ascertained as efficacious for the treatment of RR-MS; including BETASERON®, AVONEX® and REBIF®, which are derivatives of the cytokine interferon beta (IFNB), whose mechanism of action in MS is generally attributed to its immunomodulatory effects, antagonizing pro-inflammatory reactions and inducing suppressor cells.(7) Other approved drugs for the treatment of MS include Mitoxantrone and Natalizumab.

Glatiramer Acetate

Glatiramer acetate (GA) is the active substance in Copaxone®, a marketed product indicated for reduction of the frequency of relapses in patients with RRMS. Its effectiveness in reducing relapse rate and disability accumulation in RR-MS is comparable to that of other available immuno-modulating treatments.(8, 9, 10) Glatiramer acetate consists of the acetate salts of synthetic polypeptides containing four naturally occurring amino acids: L-glutamic acid, L-alanine, L-tyrosine and L-lysine. The average molecular weight of glatiramer acetate is between 5,000 and 9,000 Daltons. At a daily standard dose of 20 mg, GA is generally well tolerated; however response to the drug is variable. In various clinical trials, GA reduced relapse rates and progression of disability in patients with RR-MS. The therapeutic effect of GA is supported by the results of magnetic resonance imaging (MRI) findings from various clinical centers (11), however there are no validated predictive biomarkers of response to GA treatment.

A possible initial mode of action of GA is associated with binding to MHC molecules and consequent competition with various myelin antigens for their presentation to T cells.(12) A further aspect of its mode of action is the potent induction of T helper 2 (Th2) type cells that presumably can migrate to the brain and lead to in situ bystander suppression.(13) It has been shown that GA treatment in MS results in the induction of GA-specific T cells with predominant Th2 phenotype both in response to GA and cross-reactive myelin antigens. (13, 14) Furthermore, the ability of GA-specific infiltrating cells to express anti-inflammatory cytokines such as IL-10 and transforming growth factor-beta (TGF-β) together with brain-derived neurotrophic factor (BDNF) seem to correlate with the therapeutic activity of GA in EAE.(15, 16, 17)

Clinical experience with GA consists of information obtained from completed and ongoing clinical trials and from post-marketing experience. The clinical program includes three double-blind, placebo-controlled studies in RRMS subjects treated with GA 20 mg/day.(18, 19, 20) A significant reduction in the number of relapses, compared with placebo, was seen. In the largest controlled study, the relapse rate was reduced by 32% from 1.98 under placebo to 1.34 under GA 20 mg. GA 20 mg has also demonstrated beneficial effects over placebo on MRI parameters relevant to RRMS. A significant effect in median cumulative number of Gd-enhancing lesions over 9 months of treatment (11 lesions in the 20 mg group compared to 17 lesions under placebo) was demonstrated.

The clinical program with GA also includes one double-blind study in chronic-progressive MS subjects,(21) one double-blind placebo-controlled study in primary progressive patients,(22) one double-blind placebo-controlled study in CIS patients(23) and numerous open-label and compassionate use studies, mostly in RRMS. The clinical use of GA has been extensively reviewed and published in the current literature (24, 25, 26, 27).

However, not all treated patients respond to GA to the same extent. As the therapeutic options for MS increase, the importance of being able to determine who will respond favorably to therapy and specifically to GA, has become of increasing significance.

SUMMARY OF THE INVENTION

The present invention provides a method for treating a human subject afflicted with multiple sclerosis or a single clinical attack consistent with multiple sclerosis with a pharmaceutical composition comprising glatiramer acetate and a pharmaceutically acceptable carrier, comprising the steps of:

a) determining whether the human subject is a glatiramer acetate responder by evaluating expression of a biomarker selected from the group consisting of ERAP2, SIGLEC1, AAK1, KIAA1671, PLEKHA2, LOC730974, IFIT3, RWDD3, MYO6 SCARA3 and IFI44L, or a combination thereof, in human subject; and b) administering the pharmaceutical composition comprising glatiramer acetate and a pharmaceutically acceptable carrier to the human subject only if the human subject is identified as a glatiramer acetate responder.

The present invention also provides a method of predicting clinical responsiveness to glatiramer acetate therapy in a human subject afflicted with multiple sclerosis or a single clinical attack consistent with multiple sclerosis, the method comprising evaluating expression of a biomarker selected from the group consisting of ERAP2, SIGLEC1, AAK1, KIAA1671, PLEKHA2, LOC730974, IFIT3, RWDD3, MYO6 SCARA3 and IFI44L, or a combination thereof, in the human subject, so as to thereby predict clinical responsiveness to glatiramer acetate.

The present invention also provides a method for treating a human subject afflicted with multiple sclerosis or a single clinical attack consistent with multiple sclerosis comprising the steps of:

a) administering to the human subject a therapeutic amount of a pharmaceutical composition comprising glatiramer acetate and a pharmaceutically acceptable carrier;

b) determining whether the human subject is a glatiramer acetate responder by evaluating expression of a biomarker selected from the group consisting of ERAP2, SIGLEC1, AAK1, KIAA1671, PLEKHA2, LOC730974, IFIT3, RWDD3, MYO6 SCARA3 and IFI44L, or a combination thereof, in the human subject; and c) continuing administration of the pharmaceutical composition if the human subject is identified as a glatiramer acetate responder, or modifying the administration of the pharmaceutical composition to the human subject if the human subject is not identified as a glatiramer acetate responder.

DETAILED DESCRIPTION OF THE INVENTION

Figure 1A:
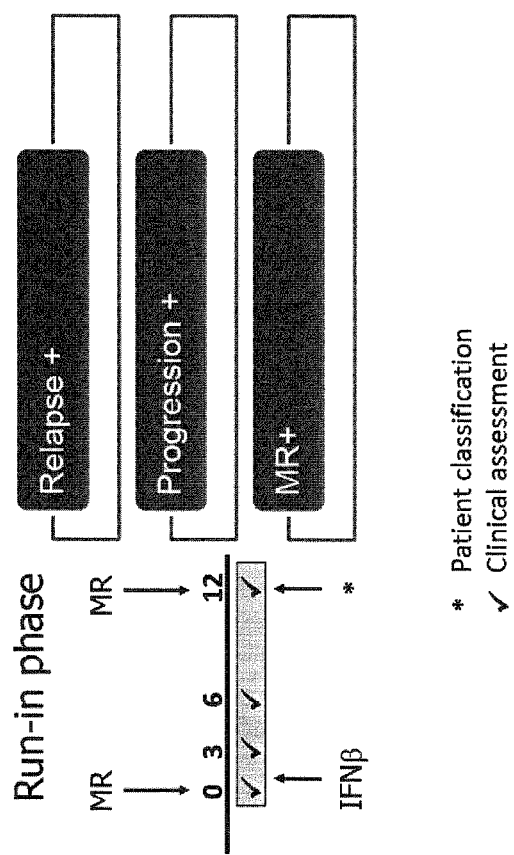
FIG. 1A: Schematic for Run-in phase of a study validating the use of diagnostic criteria for designating patient populations as Responder or Non-Responder.

The present invention provides a method for treating a human subject afflicted with multiple sclerosis or a single clinical attack consistent with multiple sclerosis with a pharmaceutical composition comprising glatiramer acetate and a pharmaceutically acceptable carrier, comprising the steps of:

c) determining whether the human subject is a glatiramer acetate responder by evaluating expression of a biomarker selected from the group consisting of ERAP2, SIGLEC1, AAK1, KIAA1671, PLEKHA2, LOC730974, IFIT3, RWDD3, MYO6 SCARA3 and IFI44L, or a combination thereof, in human subject; and d) administering the pharmaceutical composition comprising glatiramer acetate and a pharmaceutically acceptable carrier to the human subject only if the human subject is identified as a glatiramer acetate responder.

The present invention also provides a method of predicting clinical responsiveness to glatiramer acetate therapy in a human subject afflicted with multiple sclerosis or a single clinical attack consistent with multiple sclerosis, the method comprising evaluating expression of a biomarker selected from the group consisting of ERAP2, SIGLEC1, AAK1, KIAA1671, PLEKHA2, LOC730974, IFIT3, RWDD3, MYO6 SCARA3 and IFI44L, or a combination thereof, in the human subject, so as to thereby predict clinical responsiveness to glatiramer acetate.

The present invention also provides a method for treating a human subject afflicted with multiple sclerosis or a single clinical attack consistent with multiple sclerosis comprising the steps of:

d) administering to the human subject a therapeutic amount of a pharmaceutical composition comprising glatiramer acetate and a pharmaceutically acceptable carrier;

e) determining whether the human subject is a glatiramer acetate responder by evaluating expression of a biomarker selected from the group consisting of ERAP2, SIGLEC1, AAK1, KIAA1671, PLEKHA2, LOC730974, IFIT3, RWDD3, MYO6 SCARA3 and IFI44L, or a combination thereof, in the human subject; and f) continuing administration of the pharmaceutical composition if the human subject is identified as a glatiramer acetate responder, or modifying the administration of the pharmaceutical composition to the human subject if the human subject is not identified as a glatiramer acetate responder.

In some embodiments of the methods, administering the pharmaceutical composition comprising glatiramer acetate and a pharmaceutically acceptable carrier comprises administering to the human subject three subcutaneous injections of the pharmaceutical composition over a period of seven days with at least one day between every subcutaneous injection.

In some embodiments of the methods, the pharmaceutical composition is a unit dose of a 1.0 ml aqueous solution comprising 40 mg of glatiramer acetate.

In some embodiments of the methods, the pharmaceutical composition is a unit dose of a 1.0 ml aqueous solution comprising 20 mg of glatiramer acetate.

In some embodiments of the methods, the pharmaceutical composition is a unit dose of a 0.5 ml aqueous solution comprising 20 mg of glatiramer acetate.

In some embodiments of the methods, the human subject is a naive patient.

In some embodiments of the methods, the human subject has been previously administered glatiramer acetate.

In some embodiments of the methods, the human subject has been previously administered a multiple sclerosis drug other than glatiramer acetate.

In some embodiments of the methods, the human subject having a single clinical attack consistent with multiple sclerosis is a patient with at least two MRI lesions suggestive of multiple sclerosis.

In some embodiments of the methods, the human subject having a single clinical attack consistent with multiple sclerosis is a patient with at least 2 cerebral lesions detectable by an MRI scan and suggestive of multiple sclerosis.

In some embodiments of the methods, the human subject having a single clinical attack consistent with multiple sclerosis is a patient who has experienced a first clinical episode and has MRI features consistent with multiple sclerosis.

In some embodiments of the methods, the pharmaceutical composition is in a prefilled syringe for self administration by the human subject.

In some embodiments of the methods, the method comprises evaluating expression of 1, 2, 3, 4, 5, 6, 7, 8, 9, 10 or 11 of said biomarkers.

In some embodiments of the methods, the biomarker is ERAP2.

In some embodiments of the methods, the method further comprising evaluating the expression of a biomarker selected from the group consisting of SIGLEC1, AAK1, KIAA1671, PLEKHA2, LOC730974, IFIT3, RWDD3, MYO6 SCARA3 and IFI44L, or a combination thereof.

In some embodiments of the methods, the method comprises evaluating expression of 1, 2, 3, 4, 5, 6, 7, 8, 9 or 10 of said biomarkers.

In some embodiments of the methods, evaluating the expression of the biomarker comprises normalization of the subjects gene expression.

In some embodiments of the methods, evaluating the expression of the biomarker comprises comparing expression level in the human subject relative to a reference value.

In some embodiments of the methods, the reference value is based on the level of expression of the biomarker in a glatiramer acetate Non-Responder population.

In some embodiments of the methods, the reference value is based on the level of expression of the biomarker in a healthy control population.

In some embodiments of the methods, the human subject is identified as a, responder if the expression level of ERAP2, AAK1, KIAA1671, PLEKHA2, LOC730974, RWDD3, MYO6 or SCARA3 is lower than a reference value; or the expression level of SIGLEC1, IFIT3 or IFI44L is higher than a reference value.

In some embodiments of the methods, the human subject is identified as a responder if the expression level of ERAP2 is lower than a reference value.

In some embodiments of the methods, the human subject is identified as a responder if the expression level of AAK1 is lower than a reference value.

In some embodiments of the methods, the human subject is identified as a responder if the expression level of KIAA1671 is lower than a reference value.

In some embodiments of the methods, the human subject is identified as a responder if the expression level of PLEKHA2 is lower than a reference value.

In some embodiments of the methods, the human subject is identified as a responder if the expression level of LOC730974 is lower than a reference value.

In some embodiments of the methods, the human subject is identified as a responder if the expression level of RWDD3 is lower than a reference value.

In some embodiments of the methods, the human subject is identified as a responder if the expression level of MYO6 is lower than a reference value.

In some embodiments of the methods, the human subject is identified as a responder if the expression level of SCARA3 is lower than a reference value.

In some embodiments of the methods, the human subject is identified as a responder if the expression level of SIGLEC1 is higher than a reference value.

In some embodiments of the methods, the human subject is identified as a responder if the expression level of IFIT3 is higher than a reference value.

In some embodiments of the methods, the human subject is identified as a responder if the expression level of IFI44L is higher than a reference value.

In some embodiments of the methods, the expression of the biomarker is evaluated in the blood of the subject.

In some embodiments of the methods, the expression of the biomarker is evaluated in PBMCs of the subject.

In some embodiments of the methods, expression of the biomarker is evaluated at pretreatment.

In some embodiments of the methods, expression of the biomarker is evaluated after beginning treatment with glatiramer acetate.

In some embodiments of the methods, expression of the biomarker is evaluated 3 months after beginning treatment with glatiramer acetate.

In some embodiments of the methods, expression of the biomarker is evaluated 12 months after beginning treatment with glatiramer acetate.

In some embodiments of the methods, expression of the biomarker is evaluated 24 months after beginning treatment with glatiramer acetate.

In some embodiments of the methods, if the human subject is identified as a glatiramer acetate responder, the human subject is thereafter administered the pharmaceutical composition comprising glatiramer acetate and a pharmaceutically acceptable carrier as monotherapy.

In some embodiments of the methods, if the human subject is identified as a glatiramer acetate responder, the human subject is thereafter administered the pharmaceutical composition comprising glatiramer acetate and a pharmaceutically acceptable carrier in combination with another multiple sclerosis drug.

In some embodiments of the methods, if the human subject is identified as a glatiramer acetate non-responder, the human subject is thereafter administered a multiple sclerosis drug which is not glatiramer acetate.

It should be understood that all combinations of the described embodiments also are within the scope of the invention.

DEFINITIONS

Forms of Multiple Sclerosis:
 There are five distinct disease stages and/or types of MS:
 1) benign multiple sclerosis;
 2) relapsing-remitting multiple sclerosis (RRMS);
 3) secondary progressive multiple sclerosis (SPMS);
 4) progressive relapsing multiple sclerosis (PRMS); and
 5) primary progressive multiple sclerosis (PPMS).

Benign multiple sclerosis is a retrospective diagnosis which is characterized by 1-2 exacerbations with complete recovery, no lasting disability and no disease progression for 10-15 years after the initial onset. Benign multiple sclerosis may, however, progress into other forms of multiple sclerosis. Patients suffering from RRMS experience sporadic exacerbations or relapses, as well as periods of remission. Lesions and evidence of axonal loss may or may not be visible on MRI for patients with RRMS.

SPMS may evolve from RRMS. Patients afflicted with SPMS have relapses, a diminishing degree of recovery during remissions, less frequent remissions and more pronounced neurological deficits than RRMS patients. Enlarged ventricles, which are markers for atrophy of the corpus callosum, midline center and spinal cord, are visible on MRI of patients with SPMS.

PPMS is characterized by a steady progression of increasing neurological deficits without distinct attacks or remissions. Cerebral lesions, diffuse spinal cord damage and evidence of axonal loss are evident on the MRI of patients with PPMS. PPMS has periods of acute exacerbations while proceeding along a course of increasing neurological deficits without remissions. Lesions are evident on MRI of patients suffering from PRMS.(28)

A clinically isolated syndrome (CIS) is a single monosymptomatic attack compatible with MS, such as optic neuritis, brain stem symptoms, and partial myelitis. Patients with CIS that experience a second clinical attack are generally considered to have clinically definite multiple sclerosis (CDMS). Over 80 percent of patients with a CIS and MRI lesions go on to develop MS, while approximately 20 percent have a self-limited process.(29, 30) Patients who experience a single clinical attack consistent with MS may have at least one lesion consistent with multiple sclerosis prior to the development of clinically definite multiple sclerosis.

Multiple sclerosis may present with optic neuritis, blurring of vision, diplopia, involuntary rapid eye movement, blindness, loss of balance, tremors, ataxia, vertigo, clumsiness of a limb, lack of co-ordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control), impotence, diminished sexual arousal, loss of sensation, sensitivity to heat, loss of short term memory, loss of concentration, or loss of judgment or reasoning.

Relapsing Form of Multiple Sclerosis:
The term relapsing MS includes:
1) patients with RRMS;
2) patients with SPMS and superimposed relapses; and
3) patients with CIS who show lesion dissemination on subsequent MRI scans according to McDonald's criteria.

As used herein, relapsing forms of multiple sclerosis include: Relapsing-remitting multiple sclerosis (RRMS), characterized by unpredictable acute episodes of neurological dysfunction (relapses), followed by variable recovery and periods of clinical stability;

Secondary Progressive MS (SPMS), wherein patients having RRMS develop sustained deterioration with or without relapses superimposed; and Primary progressive-relapsing multiple sclerosis (PPRMS) or progressive-relapsing multiple sclerosis (PRMS), an uncommon form wherein patients developing a progressive deterioration from the beginning can also develop relapses later on.

Kurtzke Expanded Disability Status Scale (EDSS):
The Kurtzke Expanded Disability Status Scale (EDSS) is a method of quantifying disability in multiple sclerosis. The EDSS replaced the previous Disability Status Scales which used to bunch people with MS in the lower brackets. The EDSS quantifies disability in eight Functional Systems (FS) and allows neurologists to assign a Functional System Score (FSS) in each of these. The Functional Systems are: pyramidal, cerebellar, brainstem, sensory, bowel and bladder, visual & cerebral (according to www.mult-sclerosis.org/expandeddisabilitystatusscale).

Clinical Relapse:
A clinical relapse, which may also be used herein as "relapse," "confirmed relapse," or "clinically defined relapse," is defined as the appearance of one or more new neurological abnormalities or the reappearance of one or more previously observed neurological abnormalities.

This change in clinical state must last at least 48 hours and be immediately preceded by a relatively stable or improving neurological state of at least 30 days. This criterion is different from the clinical definition of exacerbation "at least 24 hours duration of symptoms," (31) as detailed in the section "relapse evaluation."

An event is counted as a relapse only when the subject's symptoms are accompanied by observed objective neurological changes, consistent with:
a) an increase of at least 1.00 in the EDSS score or one grade in the score of two or more of the seven FS (32); or,
b) two grades in the score of one of FS as compared to the previous evaluation.

The subject must not be undergoing any acute metabolic changes such as fever or other medical abnormality. A change in bowel/bladder function or in cognitive function must not be entirely responsible for the changes in EDSS or FS scores.

As used herein, "pretreatment" refers to any time point after diagnosis with MS or CIS and before beginning of treatment with a composition comprising GA.

As used herein, a "multiple sclerosis drug" is a drug or an agent intended to treat clinically defined MS, CIS, any form of neurodegenerative or demyelinating diseases, or symptoms of any of the above mentioned diseases. "Multiple sclerosis drugs" may include but are not limited to antibodies, immunosuppressants, anti-inflammatory agents, immunomodulators, cytokines, cytotoxic agents and steroids and may include approved drugs, drugs in clinical trial, or alternative treatments, intended to treat clinically defined MS, CIS or any form of neurodegenerative or demyelinating diseases. "Multiple sclerosis drugs" include but are not limited to Interferon and its derivatives (including BETASERON®, AVONEX® and REBIF®), Mitoxantrone and Natalizumab. Agents approved or in-trial for the treatment of other autoimmune diseases, but used in a MS or CIS patient to treat MS or CIS are also defined as multiple sclerosis drugs.

As used herein, a "naïve patient" is a subject that has not been treated with any multiple sclerosis drugs as defined in the former paragraph.

As used herein, "in the blood of the subject" is represented by PBMCs, lymphocytes, monocytes, macrophages, basophils, dendritic cells or other cells derived from the subject's blood.

As used herein "3 months" refers to a time point which is three months after the beginning of administration of a pharmaceutical composition to a subject. "12 months" refers to a time point which is twelve months after the beginning of administration of a pharmaceutical composition to a subject. "24 months" refers to a time point which is twenty four months after the beginning of administration of a pharmaceutical composition to a subject.

As used herein a "reference value" is a value or range of values that characterizes a specified population in a defined state of health.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Figure 1B:
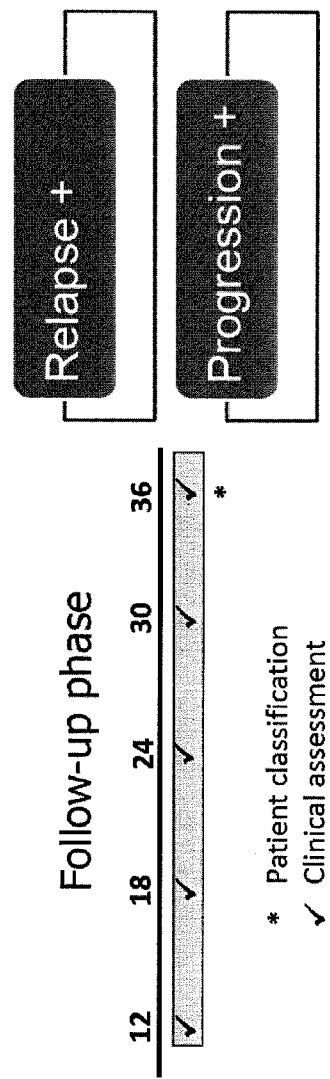
FIG. 1B: Schematic for Follow-up phase of a study validating the use of diagnostic criteria for designating patient populations as Responder or Non-Responder.

Identification of Patients as Responders and GA Non-Responders is Indicative of Future Activity During a run-in phase, patients were evaluated at baseline, 3 months, 6 months and 12 months and were scored positive or negative on the basis of three criteria: relapse, disease progression, and MRI evaluation (FIG. 1a). During the Follow-up phase patients were evaluated at 12 months, 18 months, 24 months, 30 months and 36 months and were scored positive or negative on the basis of two criteria: relapse and disease progression (FIG. 1b). Table 1 shows odds ratio, confidence limits and significance of follow-up phase progression in patients having one, two or three positive variables during run-in phase classification (33).

TABLE 1

Risk of activity during the period of follow-up (months 12-36) according to the positivity for the different variables after 12 months of therapy.

| | Odds ratio (CI) | Significance |
|---|---|---|
| One positive variable | 1.4 (0.7-2.6) | 0.3 |
| Two positive variables | 5.9 (2.5-15.6) | <0.0001 |
| Three positive variables | 13.2 (2.9-125.7) | 0.0003 |

Example 2

Identification of Patients as GA Responders and Non-Responders

Figure 2:
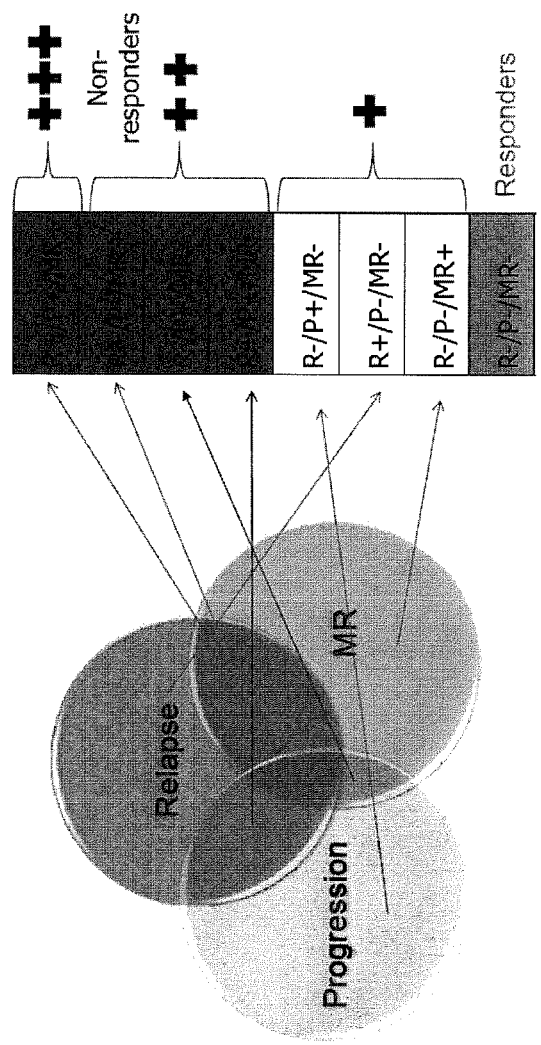
FIG. 2: Schematic for the use of observation criteria for the identification of Responder and Non-Responder populations.

Similar to Example 1, above, patients were treated with glatiramer acetate and evaluated at baseline, 3 months, 12 months and 24 months after beginning treatment with glatiramer acetate and were scored positive or negative on the basis of three criteria: relapse, disease progression, and MRI evaluation (FIG. 2). Patients scoring positive in at least two variables were classified as Non-Responders while those scoring negative in all three variables were classified as Responders.

TABLE 2

Characteristics of patient subgroups.

| Characteristics | Responders | Non-responders | HC |
|---|---|---|---|
| N | 6 | 9 | 14 |
| Age (years)[a] | 30.2 (5.8) | 36.4 (8.6) | 29.9 (4.7) |
| Female/male (% women) | 6/0 (100.0) | 6/3 (66.7) | 10/4 (71.4) |
| Duration of disease (years)[a] | 5.7 (3.7) | 8.4 (5.4) | — |
| EDSS[b] | 1.5 (1.5-1.5) | 2.1 (1.3-2.8) | — |
| Number of relapses the two previous years[a] | 2.0 (0) | 2.6 (0.5) | — |

[a]Data are expressed as mean (standard deviation).
[b]Data are expressed as mean (interquartile range).
HC: healthy controls Example 3

Figure 3:
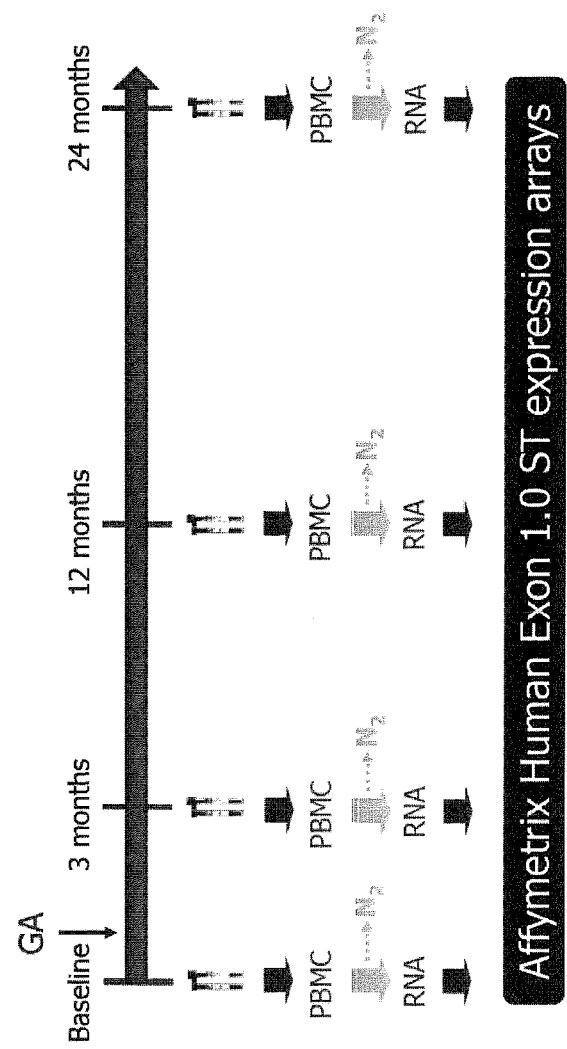
FIG. 3: Schematic for the study identifying differentially expressed genes in GA Responder and Non-Responder populations.

Identification of Differentially Expressed Genes in Patients Identified as Responders Versus Non-Responders Methods Subjects and Cells:

Relapsing-remitting multiple sclerosis patients were treated with GA. Whole blood was taken from patients at four time points including baseline (baseline, month 3, month 12 and month 24). Peripheral blood mononuclear cells (PBMCs) were cryopreserved and RNA was isolated for gene expression analysis (FIG. 3).

Gene Expression Analysis

Gene expression analysis was performed using Affymetrix Human Exon 1.0 ST expression arrays. Preprocessing was performed with an integrated three-step approach: background correction, normalization (iterPLER), and summarization (Sketch-Quantile) implemented in the Affymetrix Expression Console. Batch effects normalization was performed with the removeBatchEffect function from limma R package.

The selection of differentially expressed genes (DEG) between responders and non-responders at baseline was based on a linear model analysis with empirical Bayes moderation of the variance estimates. P-values were adjusted to obtain control over the false discovery rate (FDR).

Results 277 genes were identified as differentially expressed (p<0.01) at baseline.

TABLE 3

Expression levels of differentially expressed genes
in Responder (R) and Non-Responder (NR) populations (log)

| Symbol | Name | p value | FDR | R | NR |
|---|---|---|---|---|---|
| ERAP2 | endoplasmic reticulum aminopeptidase 2 | $3 \times 10^{-5}$ | 0.67 | 6.25 | 6.90 |
| SIGLEC1 | sialic acid binding Ig-like lectin 1, sialoadhesin | 0.0001 | 0.67 | 5.65 | 4.71 |
| AAK1 | AP2 associated kinase 1 | 0.0002 | 0.67 | 2.88 | 3.74 |
| KIAA1671 | KIAA1671 | 0.0002 | 0.67 | 4.80 | 5.30 |
| PLEKHA2 | pleckstrin homology domain containing, family A (phosphoinositide binding specific) member 2 | 0.0003 | 0.67 | 6.68 | 6.98 |
| LOC730974 | similar to slowmo homolog 2 | 0.0004 | 0.67 | 4.07 | 4.47 |
| IFIT3 | interferon-induced protein with tetratricopeptide repeats 3 | 0.0004 | 0.67 | 5.79 | 5.14 |
| RWDD3 | RWD domain containing 3 | 0.0004 | 0.67 | 4.11 | 4.54 |
| MYO6 | myosin VI | 0.0006 | 0.67 | 3.39 | 3.80 |
| SCARA3 | scavenger receptor class A, member 3 | 0.0006 | 0.67 | 5.82 | 6.15 |
| IFI44L | interferon-induced protein 44-like | 0.0007 | 0.67 | 6.63 | 5.80 |
| ... | ... | ... | ... | ... | ... |

At baseline, GA Responders had reduced levels of expression of ERAP2, AAK1, KIAA1671, PLEKHA2, LOC730974, RWDD3, MYO6 and SCARA3 and increased levels of SIGLEC1, IFIT3 and IFI44L relative to GA Non-Responders.

Further investigation focused on the expression of ERAP2 in Responder populations as compared to Non-Responders and Healthy Controls both at baseline and at several time-points after beginning administration of GA.

Figure 4:
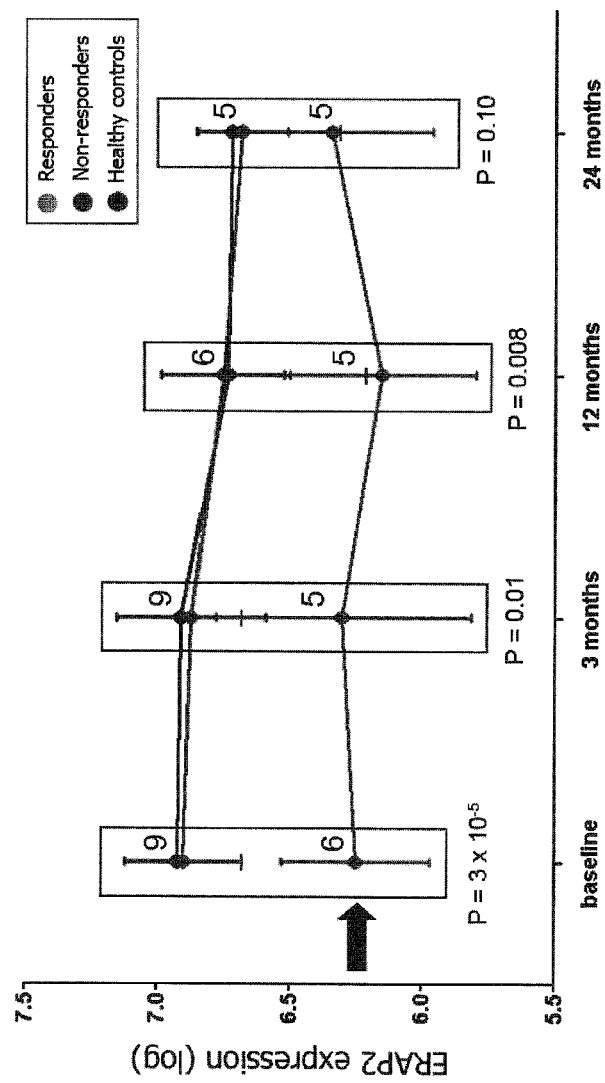
FIG. 4: Expression of ERAP 2 in PBMC of Responder and Non-Responder populations and healthy controls.

Expression Levels of ERAP2 were lower in Responders than in Non-Responders and did not significantly change over the course of treatment (FIG. 4).

Figure 5A:
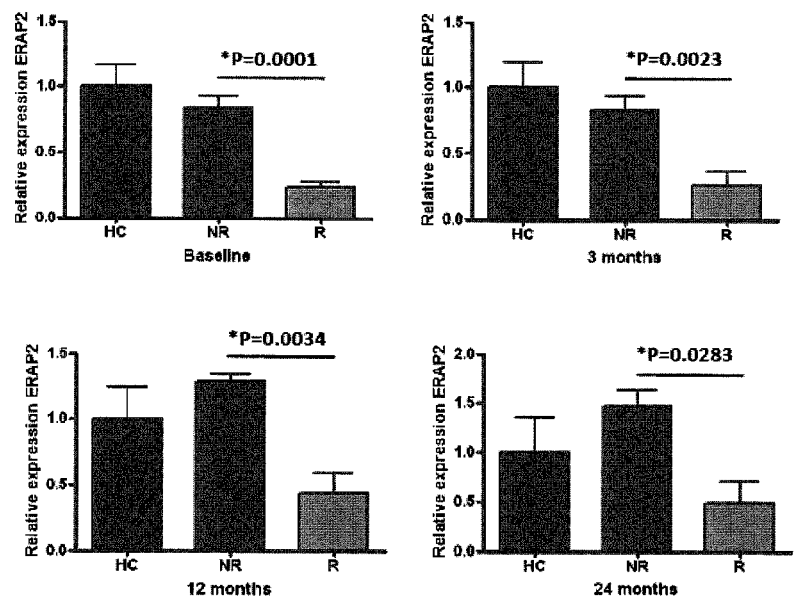
FIG. 5A: PCR validation showing reduced expression of ERAP2 in GA Responders.
Figure 5B:
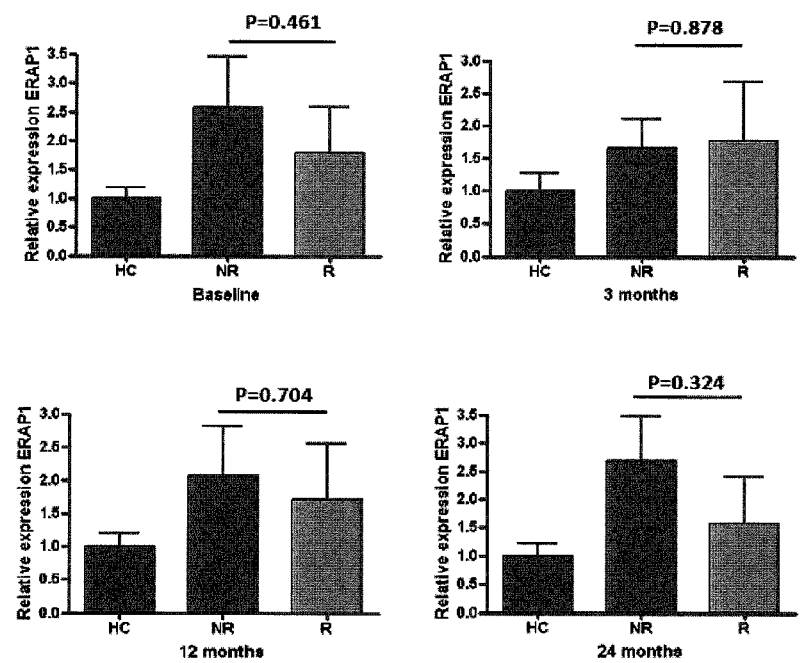
FIG. 5B: PCR validation showing no change of expression for ERAP1 in GA Responders.

PCR analysis was performed in order to validate the expression of ERAP2 in Responder populations as compared to Non-Responders and Healthy Controls. The expression of ERAP2 was significantly reduced, as compared to expression in Non-Responder populations at all time points tested. In contrast, expression of ERAP1 did not differ significantly between the two populations at any time point R (n=4)/NR (n=7)/HC (n=11) (FIG. 5).

Figure 6:
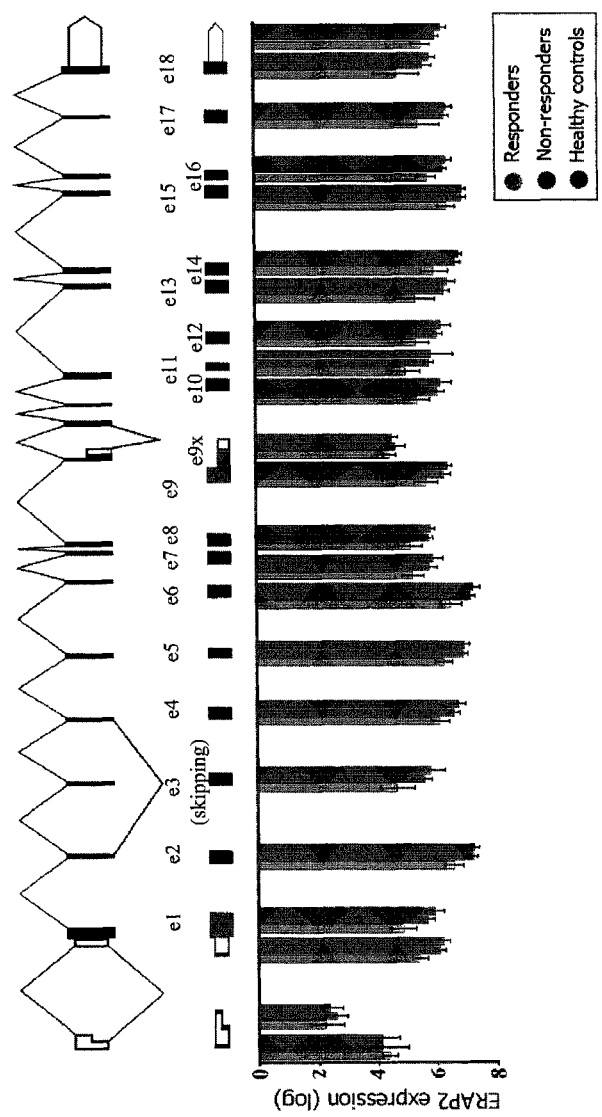
FIG. 6: Exon level analysis of ERAP2 expression in Responder and Non-Responder populations and healthy controls.

An exon level analysis revealed that expression of all exons of ERAP2 were reduced in GA Responders as compared to GA Non-Responders and healthy controls (FIG. 6).

Discussion

The present study identifies biomarkers that are differentially expressed genes associated with response to GA in patients with RRMS. For this study, PBMC were obtained at baseline, 3 months 12 months and 24 months after administration of glatiramer acetate. The findings demonstrate that the differentially expressed genes identified here are useful as biomarkers of response for GA. This transcriptomic study in GA Responders and Non-Responders identified of numerous potential response biomarkers; including ERAP2.

ERAP2 is and ER aminopeptidase involved in trimming of peptides for antigen presentation by HLA I molecules. ERAP2 expression was reduced at baseline (Table 2), remained reduced relative to Non-Responders and healthy controls (FIG. 5) and was not modified by glatiramer acetate treatment (FIG. 4). Accordingly, ERAP2 is useful as a biomarker to predict GA response both prior and subsequent to administration of GA.

The finding that GA Responders had reduced levels of expression of ERAP2, AAK1, KIAA1671, PLEKHA2, LOC730974, RWDD3, MYO6 and SCARA3 and increased levels of SIGLEC1, IFIT3 and IFI44L relative to GA Non-Responders at baseline is significant because the subject need not begin therapy in order to determine status as a Responder or Non-Responder.

Example 4

Identification of MS Patients as GA Responders or GA Non-Responders

Methods

A subject afflicted with multiple sclerosis or a single clinical attack consistent with multiple sclerosis is evaluated to determine if the subject is a GA Responder or a GA Non-Responder. Levels of expression of one or more of the differentially expressed genes described herein are evaluated for the subject and compared relative to a reference value.

Results

The expression level of ERAP2, AAK1, KIAA1671, PLEKHA2, LOC730974, RWDD3, MYO6 or SCARA3 is decreased in a GA Responder relative to a GA Non-Responder. The expression level of SIGLEC1, IFIT3 or IFI44L is increased in a GA Responder relative to a GA Non-Responder.

Subjects identified as GA Responders are thereafter treated with a pharmaceutical composition comprising glatiramer acetate as an active ingredient, and benefit from the treatment. Subjects identified as GA Non-Responders are thereafter treated with a multiple sclerosis drug other than glatiramer acetate.

REFERENCES

1. Noseworthy J H, Lucchinetti C, Rodriguez M, Weinshenker B G. Multiple sclerosis. N Engl J Med 2000; 343:938-52.
2. Guideline on clinical investigation of medicinal products for the treatment of multiple sclerosis EMEA, London 16 Sep. 2006.
3. Bjartmar C, Fox R J. Pathological mechanisms and disease progression of multiple sclerosis: therapeutic implications. Drugs of Today 2002; 38:17-29.
4. Fleming J O. Diagnosis and management of multiple sclerosis. 1st ed. New York: Professional communications, Inc., 2002.
5. Anderson D W, Ellenberg J H, Leventhal C M et al. Revised estimate of the prevalence of multiple sclerosis in the United States. Ann Neurol 1992; 31:333-36.
6. Compston A, Lassmann H, McDonald I. The story of multiple sclerosis. In: Compston A, Confavreux C, Lassman H, Mcdonald I, Miller D, Noseworthy J H, Smith K, Wekerle H, editors. McAlpine's Multiple Sclerosis. London: Churchill Livingstone; 2006. p. 3-68.

7. Revel M., Pharmacol. Ther., 100(1):49-62 (2003).
8. Martinelli B F, Rovaris M, Johnson K P, Miller A, Wolinsky J S, Ladkani D, Shifroni G, Comi G, Filippi M. Effects of glatiramer acetate on relapse rate and accumulated disability in multiple sclerosis: meta-analysis of three double-blind, randomized, placebo-controlled clinical trials. Mult Scler. 2003 August; 9(4):349-55.
9. Mikol D D, Barkhof F, Chang P, Coyle P K, Jeffery D R, Schwid S R, Stubinski B, Uitdehaag B M; REGARD study group. Lancet Neurol. 2008 October; 7(10):903-14. Epub 2008 Sep. 11.
10. BECOME TRIAL, Presented at the 23rd Congress of the European Committee for Treatment and Research in Multiple Sclerosis (ECTRIMS) in Prague, Czech Republic.
11. Comi G, Filippi M and Wolinsky J S. European/Canadian multi-center, double-blind randomized, placebo controlled study of the effects of glatiramer acetate on magnetic resonance imaging-measured disease activity and burden in patients with relapsing-remitting multiple sclerosis. Ann Neurol 2001; (49):290-297.
12. Fridkis H M, Aharoni R, Teitelbaum D, Arnon R, Sela M, Strominger J L. Binding of random copolymers of three amino acids to class II MHC molecules. Int. Immunol. 1999 May; 11(5):635-41.
13. Dhib-Jalbut S S, Zhan M, Johnson K P, Martin R. Glatiramer acetate reactive blood mononuclear cells respond to myelin antigens with a Th-2 biased phenotype. J Neuroimmunology 2003; 140:163-171.
14. Chen M, Gran B, Costello K, Johnson K P, Martin R, Dhib-Jalbut S. Glatiramer acetate induces a Th-2 biased response and cross-reactivity with myelin basic protein in patients with MS. Multiple Sclerosis 2001; 7:209-219.
15. Weber M S, Prod'homme T, Youssef S, Dunn S E, Rundle C D, Lee L, Patarroyo J C, Stüve O, Sobel R A, Steinman L, Zamvil S S. Type II monocytes modulate T cell-mediated central nervous system autoimmune disease. Nat Med (2007) 13:935-943.
16. Aharoni R, Kayhan B, Eilam R, Sela M, and Arnon R. Glatiramer acetate-specific T cells in the brain express T helper 2/3 cytokines and brain-derived neurotrophic factor in situ. PNAS August 2003; 100(24):14157-62.
17. Sarchielli P, Zaffaroni M, Floridi A, Greco L, Candeliere A, Mattioni A, Tenaglia S, Di Filippo M, Calabresi P. Production of brain-derived neurotrophic factor by mononuclear cells of patients with multiple sclerosis treated with glatiramer acetate, interferon-beta 1a, and high doses of immunoglobulins. Mult Scler 2007 April; 13(3):313-31. Epub 2007 Jan. 29.
18. Bornstein, M B, Miller, A, Slagle, S, et al. A pilot trial of Cop 1 in exacerbating remitting multiple sclerosis. *New Eng J Med* 1987; 317: 408-14.
19. Comi, G, Fillippi, M, Wolinsky, J S, et al. European/Canadian multicenter, double-blind, randomized, placebo-controlled study of the effects of glatiramer acetate on magnetic resonance imagine-measured disease activity and burden in patients with relapsing multiple sclerosis. *Ann Neural* 2001; 49: 290-7.
20. Johnson, K P, Brooks, B R, Cohen, J A, et al. Extended use of glatiramer acetate (Copaxone) is well tolerated and maintains its clinical effect on multiple sclerosis relapse rate and degree of disability. Neurology 1998; 50:701-8.
21. Bornstein, M B, Miller, A, Slagle, S, at al. A placebo-controlled, double-blind, randomized, two-center, pilot trial of Cop-1 in chronic progressive multiple sclerosis. *Neurology* 1991; 41: 533-39.
22. Wolinsky, J S, Narayana, P A, O'Conner, P, et al. Glatiramer acetate in primary progressive multiple sclerosis: Results of a multinational, multicenter, double-blind, placebo-controlled trial. *Ann Neurol* 2007; 61:14-24.
23. Comi G, Filippi M, Treatment with glatiramer acetate delays conversion to clinically definite multiple sclerosis (CDMS) in patients with clinically isolated syndromes (CIS). *Neurology* 2008; 71 (2): 153.
24. Tselis, A, Khan, O, Lisak, R P, Glatiramer acetate in the treatment of multiple sclerosis. *Neuropsychiatric Dis Treat* 2007; 3(2):259-67.
25. Wolinsky, J S, The use of glatiramer acetate in the treatment of multiple sclerosis. *Adv Neurol* 2006; 273-92.
26. Comi G, Cohen J A, Filippi M, Results from a phase III, one-year, randomized, double-blind, parallel-group, dose-comparison study with glatiramer acetate in relapsing-remitting multiple sclerosis. *Mult Scler* 2008; 14(suppl 1):S299.
27. Comi G, Filippi M. Presented at: 60th Annual Meeting of the American Academy of Neurology: April 12-19; Chicago, Ill. Abstract LBS.003.
28. Johnson D, Hafler D A, Fallis R J, Lees M B, Brady R O, Quarles R H, Weiner H L., "Cell-mediated immunity to myelin-associated glycoprotein, proteolipid protein, and myelin basic protein in multiple sclerosis.", *J Neuroimmunol.* 1986 November; 13 (1):99-108.
29. Brex P A et al., "A longitudinal study of abnormalities on MRI and disability from multiple sclerosis", *N Engl J Med* 2002 Jan. 17, 346(3):158-64.
30. Frohman E M et al., "The utility of MRI in suspected MS: report of the Therapeutics and Technology Assessment Subcommittee of the American Academy of Neurology", *Neurology,* 2003, Sep. 9, 61(5):602-11.
31. Poser C M. et al. New diagnostic criteria for multiple sclerosis: Guidelines for research protocols. Ann. Neurol., 13(3): 227-31, 1983
32. Neurostatus, slightly modified from J. F. Kurtzke Neurology 1983:33, 1444-52; L. Kappos, Dept. of Neurology, University Hospital, CH-4031/Basel, Switzerland.
33. Rio, J. et al., Measures in the first year of therapy predict the response to interferon β in MS, Multiple Sclerosis, 15: 848-853, 2009.

What is claimed is:

1. A method for treating a human subject afflicted with multiple sclerosis or a single clinical attack consistent with multiple sclerosis with a pharmaceutical composition comprising glatiramer acetate and a pharmaceutically acceptable carrier, comprising administering the pharmaceutical composition to a human subject identified as a glatiramer acetate responder if the expression level of a biomarker selected from the group consisting of ERAP2, AAK1, KIAA1671, PLEKHA2, LOC730974, RWDD3, MYO6 and SCARA3 is lower than a reference value, or if the expression level of a biomarker selected from the group consisting of SIGLEC1, IFIT3 and IFI44L is higher than a reference value.

2. A method for treating a human subject afflicted with multiple sclerosis or a single clinical attack consistent with multiple sclerosis comprising the steps of:
 a) administering to the human subject a therapeutic amount of a pharmaceutical composition comprising glatiramer acetate and a pharmaceutically acceptable carrier;
 b) evaluating expression of a biomarker selected from the group consisting of ERAP2, SIGLEC1, AAK1, KIAA1671, PLEKHA2, LOC730974, IFIT3, RWDD3, MYO6 SCARA3 and IFI44L, or a combination thereof, in the human subject; and c) continuing administration of the pharmaceutical composition if the human subject is identified as a glatiramer acetate responder based on the expression level of a biomarker selected from the group consisting of ERAP2, AAK1, KIAA1671, PLEKHA2, LOC730974, RWDD3, MYO6 and SCARA3 being lower than a reference value, or the expression level of a biomarker selected from the group consisting of SIGLEC1, IFIT3 and IFI44L being higher than a reference value, or modifying the administration of the pharmaceutical composition to the human subject if the human subject is not identified as a glatiramer acetate responder.

3. The method of claim 1, wherein administering the pharmaceutical composition comprising glatiramer acetate and a pharmaceutically acceptable carrier comprises administering to the human subject three subcutaneous injections of the pharmaceutical composition over a period of seven days with at least one day between every subcutaneous injection.

4. The method of claim 1, wherein the pharmaceutical composition is a unit dose of a 1.0 ml aqueous solution comprising 40 mg of glatiramer acetate, a unit dose of a 1.0 ml aqueous solution comprising 20 mg of glatiramer acetate or a unit dose of a 0.5 ml aqueous solution comprising 20 mg of glatiramer acetate.

5. The method of claim 1, wherein the human subject is a naive patient, or has been previously administered a multiple sclerosis drug other than glatiramer acetate.

6. The method of claim 1, wherein the human subject having a single clinical attack consistent with multiple sclerosis is a patient with at least two MRI lesions suggestive of multiple sclerosis, a patient with at least 2 cerebral lesions detectable by an MRI scan and suggestive of multiple sclerosis, or a patient who has experienced a first clinical episode and has MRI features consistent with multiple sclerosis.

7. The method of claim 1, wherein the pharmaceutical composition is in a prefilled syringe for self administration by the human subject.

8. The method of claim 1, wherein the expression of 2, 3, 4, 5, 6, 7, 8, 9, 10 or 11 of said biomarkers are evaluated.

9. The method of claim 1, wherein the biomarker is ERAP2.

10. The method of claim 9, wherein the expression of 1, 2, 3, 4, 5, 6, 7, 8, 9 or 10 additional biomarkers selected from the group consisting of SIGLEC1, AAK1, KIAA1671, PLEKHA2, LOC730974, IFIT3, RWDD3, MYO6, SCARA3 and IFI44L, or a combination thereof are evaluated.

11. The method of claim 2, wherein evaluating the expression of the biomarker comprises normalization of the subjects gene expression.

12. The method of claim 1, wherein the reference value is based on the level of expression of the biomarker in a glatiramer acetate Non-Responder population or the level of expression of the biomarker in a healthy control population.

13. The method of any one of claim 1, wherein the expression of the biomarker is evaluated in the blood of the subject or in PBMCs of the subject.

14. The method of claim 1, wherein expression of the biomarker is evaluated at pretreatment.

15. The method of claim 1, wherein expression of the biomarker is evaluated after beginning treatment with glatiramer acetate.

16. The method of claim 15, wherein expression of the biomarker is evaluated 3 months after beginning treatment with glatiramer acetate, 12 months after beginning treatment with glatiramer acetate or 24 months after beginning treatment with glatiramer acetate.

17. The method of claim 1, wherein the human subject is thereafter administered the pharmaceutical composition comprising glatiramer acetate and a pharmaceutically acceptable carrier as monotherapy.

18. The method of claim 2, wherein the reference value is based on the level of expression of the biomarker in a glatiramer acetate Non-Responder population or the level of expression of the biomarker in a healthy control population.

19. The method of claim 2, wherein the biomarker is ERAP2.

* * * * *